United States Patent [19]

Edwards et al.

[11] Patent Number: 5,685,839
[45] Date of Patent: Nov. 11, 1997

[54] ULTRASOUND PROBE WITH THERMAL SENSING

[76] Inventors: Stuart D. Edwards, 1681 Austin Ave., Los Altos, Calif. 94024; Ronald G. Lax, 10724 Glenbrook Estates Ct., Grassvalley, Calif. 95945; Ingemar H. Lundquist, P.O. Box 1186, 17 Mile Dr. at the Dunes Rd., Pebble Beach, Calif. 93953; Hugh R. Sharkey, 654 Iris St., Redwood City, Calif. 94061; James A. Baker, 4292-P Wilkie Way, Palo Alto, Calif. 94306

[21] Appl. No.: 439,191

[22] Filed: May 11, 1995

Related U.S. Application Data

[60] Division of Ser. No. 180,511, Jan. 12, 1994, which is a continuation-in-part of Ser. No. 929,638, Aug. 12, 1982, abandoned, which is a continuation-in-part of Ser. No. 12,370, Feb. 2, 1993, Pat. No. 5,370,675, which is a continuation-in-part of Ser. No. 62,364, May 13, 1993, Pat. No. 5,435,805, which is a continuation-in-part of Ser. No. 61,072, May 14, 1993, Pat. No. 5,385,544, which is a continuation-in-part of Ser. No. 61,647, May 13, 1993, Pat. No. 5,421,819.

[51] Int. Cl.$^6$ .................................................... A61B 17/00
[52] U.S. Cl. ............................................................ 604/22
[58] Field of Search ................................. 604/19–22, 53, 604/164, 280; 606/39, 32, 45; 607/96, 113, 115, 116, 138, 156, 101, 102, 97–99

[56] References Cited

U.S. PATENT DOCUMENTS

| | | | |
|---|---|---|---|
| 4,641,649 | 2/1987 | Walinsky et al. | 128/303.1 |
| 4,776,334 | 10/1988 | Prionas | 128/303.1 |
| 4,998,932 | 3/1991 | Rosen et al. | 606/29 |
| 5,277,201 | 1/1994 | Stern | 607/98 |

FOREIGN PATENT DOCUMENTS

| | | | |
|---|---|---|---|
| 0324368 | 5/1936 | Italy | 607/99 |
| 0196477 | 6/1938 | Switzerland | 607/99 |

*Primary Examiner*—Manuel Mendez
*Attorney, Agent, or Firm*—Flehr Hohbach Test Albritton & Herbert LLP

[57] ABSTRACT

A medical probe apparatus comprising a catheter having a stylet guide housing with one or more stylet ports therein and stylet guides for directing one or more flexible stylets outward through respective stylet ports and through intervening tissue to target tissue. The active stylets emit radio frequency RF energy which establishes an RF current in the patient. The current, being densest at the stylet tips, causes heating of the surrounding tissue to initiate ablation of the target tissue. One aspect of the invention includes temperature sensing stylets at the location of the RF emitting stylets to monitor the temperature of the tissue being ablated. This allows the surgeon to have increased knowledge about the abating action under way in order to control the intensity of the applied RF current, or to adjust the amount of time the current is applied, or both. Further included herein is a plurality of temperature sensors mounted on an ultrasound probe to be used to monitor tissue temperature at the ultrasound probe while allowing the ultrasound device to monitor the position and orientation of the medical probe apparatus of the present invention.

11 Claims, 8 Drawing Sheets

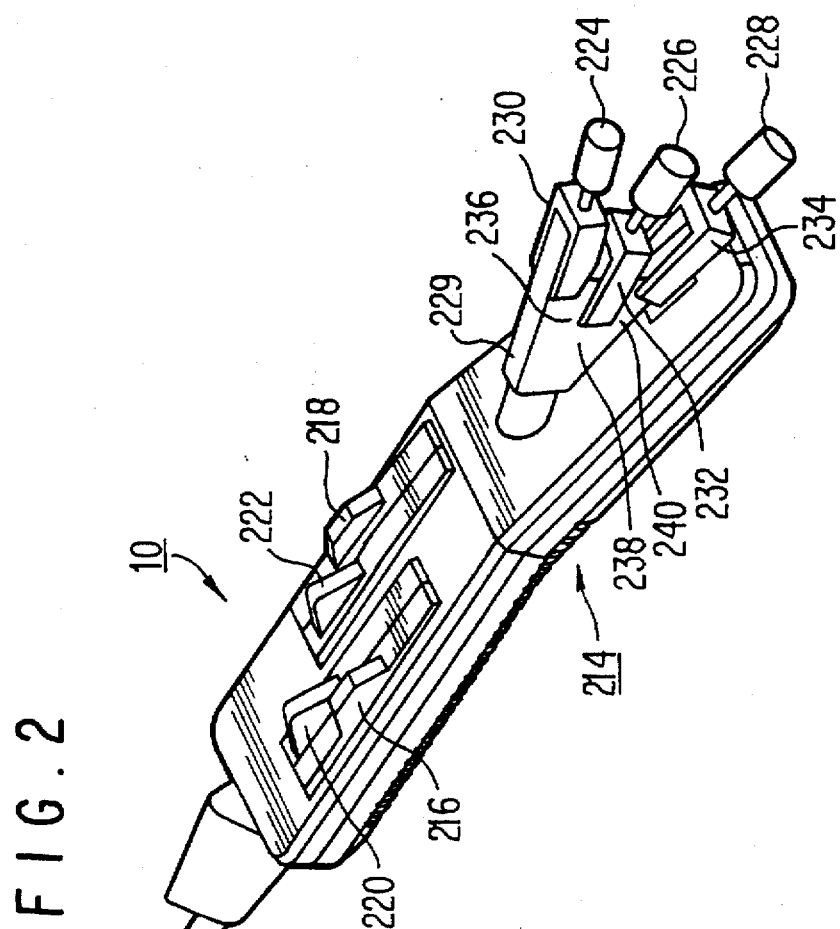
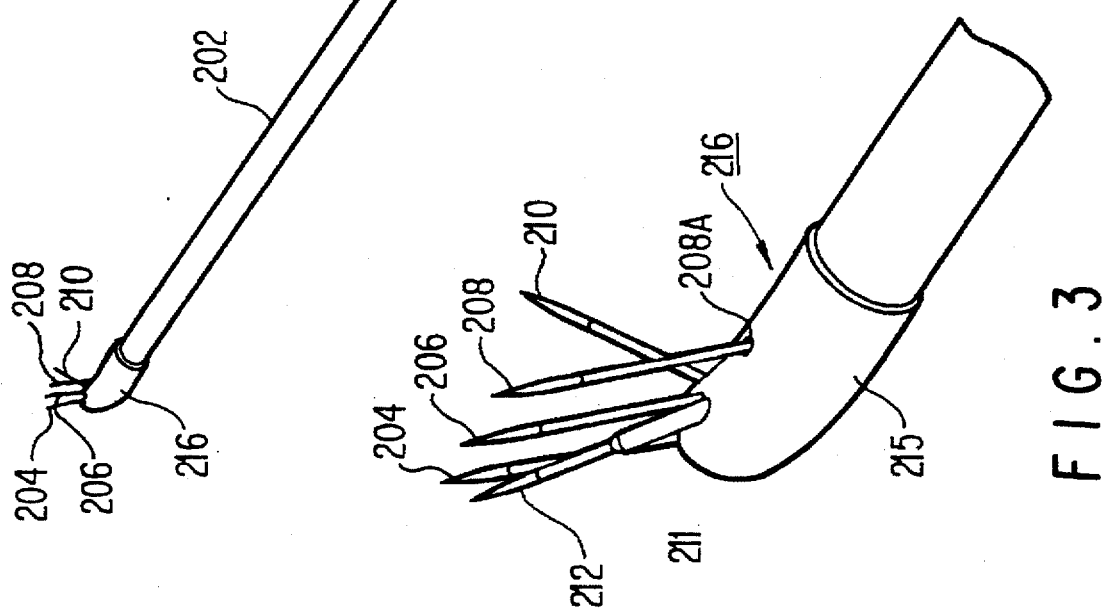

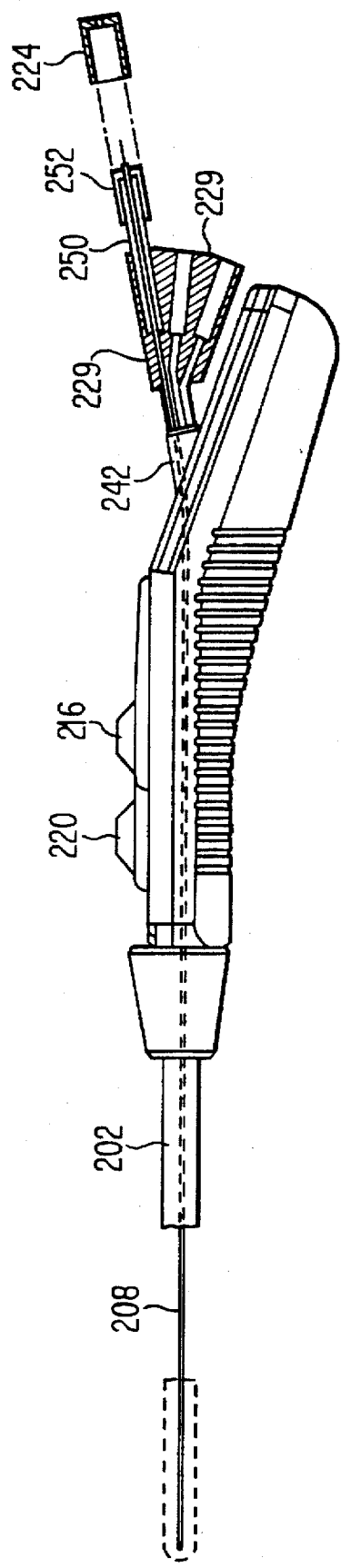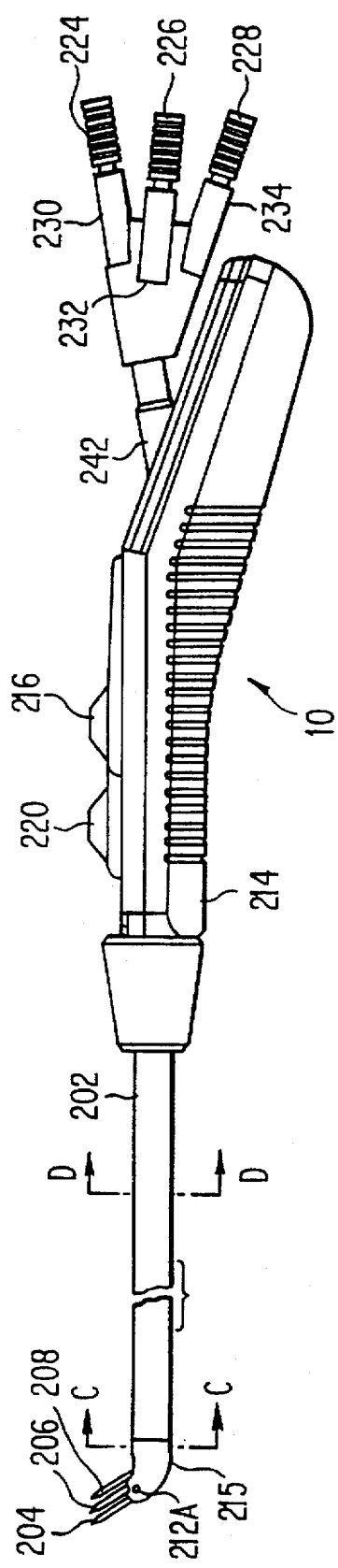

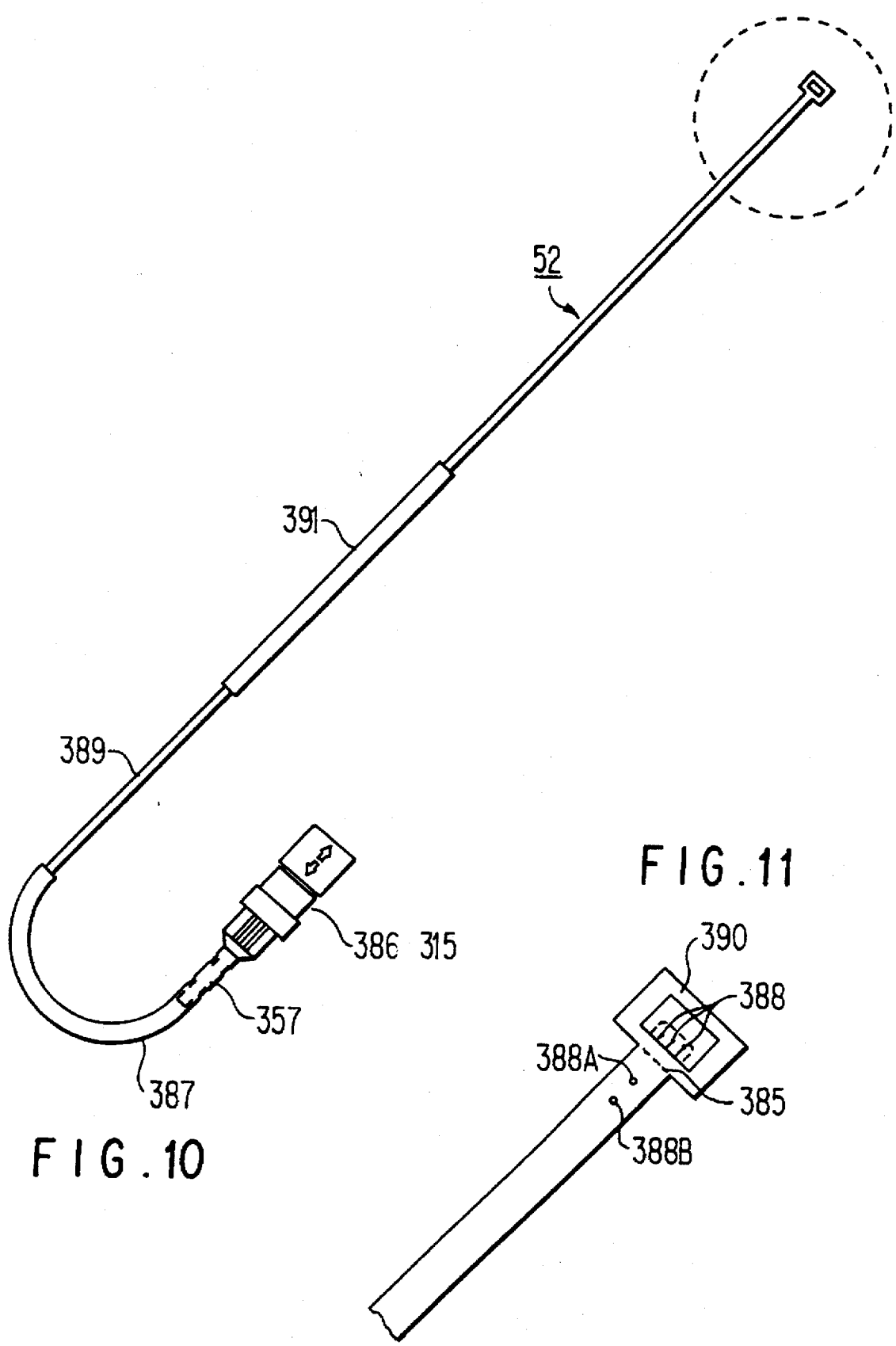

ULTRASOUND PROBE WITH THERMAL SENSING

RELATIONSHIP TO COPENDING APPLICATIONS

This is a division of Ser. No. 08/180,511 filed Jan. 12, 1994 and still pending which is a continuation-in-part of application Ser. No. 07/929,638 filed Aug. 12, 1992, now abandoned; which is a Continuation In Part of Ser. No. 08/012,370 filed Feb. 2, 1993, now U.S. Pat. No. 5,370,675; which is a Continuation In Part of Ser. No. 08/062,364 filed May 13, 1993, now U.S. Pat. No. 5,385,544; which is a Continuation In Part of Ser. No. 08/061,072 filed May 14, 1993, now U.S. Pat. No. 5,385,544, which is a Continuation In Part of Ser. No. 08/061,647 filed May 13, 1993 and now U.S. Pat. No. 5,421,819. The entire contents of all of the above applications are incorporated herein by reference.

FIELD OF THE INVENTION

This invention is directed to unique apparatus and methods for penetrating body tissues for medical purposes such as tissue ablation and fluid substance delivery, for example. The device penetrates tissue to the precise target selected in order to deliver energy to the tissue and/or deliver substances. It limits this treatment to the precise preselected site, thereby minimizing trauma to normal surrounding tissue and achieving a greater medical benefit. This device is a catheter-like device for positioning a treatment assembly in the area or organ selected for medical treatment with one or more stylets in the catheter, mounted for extension from a stylet port or ports in the side of the catheter through surrounding tissue to the tissue targeted for medical intervention.

In particular, this invention is directed to a medical probe device including additional stylet probes for extension from additional stylet ports into the target tissue to measure the temperature of the target tissue to monitor the progress and effectiveness of the ablation process under way. Together with the use of an ultrasound probe, additional information is made available to the surgeon for accurate use for and treatment of a patient.

BACKGROUND OF THE INVENTION

Treatment of cellular tissues generally requires direct contact of target tissue with a medical instrument, usually by surgical procedures exposing both the target and intervening tissue to substantial trauma. Often, precise placement of a treatment probe is difficult because of the location of targeted tissues in the body or the proximity of the target tissue to easily damaged, critical body organs, nerves, or other components.

Benign prostatic hypertrophy or hyperplasia (BPH), for example, is one of the most common medical problems experienced by men over 50 years old. Urinary tract obstruction due to prostatic hyperplasia has been recognized since the earliest days of medicine. Hyperplastic enlargement of the prostate gland often leads to compression of the urethra, resulting in obstruction of the urinary tract and the subsequent development of symptoms including frequent urination, decrease in urinary flow, nocturia, pain, discomfort, and dribbling. The association of BPH with aging has been shown by the incidence of BPH in 50 percent of men over 50 years of age and increases in incidence to over 75 percent in men over 80 years of age. Symptoms of urinary obstruction occur most frequently between the ages of 65 and 70 when approximately 65 percent of men in this age group have prostatic enlargement.

Currently there is no nonsurgical method for treating BPH which has proven to be effective. In addition, the surgical procedures available are not totally satisfactory. Currently, patients suffering from the obstructive symptoms of this disease are provided with few options: continue to cope with the symptoms (i.e., conservative management), submit to drug therapy at early stages, or submit to surgical intervention. More than 430,000 patients per year in the United States undergo surgery for removal of prostatic tissue. These represent less than five percent of men exhibiting clinical significant symptoms.

Those suffering from BPH are often elderly men, many with additional health problems which increase the risk of surgical procedures. Surgical procedures for the removal of prostatic tissue are associated with a number of hazards including anesthesia related morbidity, hemorrhage, coagulopathies, pulmonary emboli, and electrolyte imbalances. These procedures performed currently can also lead to cardiac complications, bladder perforation, incontinence, infection, urethral or bladder neck stricture, retention of prostatic chips, retrograde ejaculation, and infertility. Due to the extensive invasive nature of the current treatment options for obstructive uropathy, the majority of patients delay definitive treatment of their condition. This circumstance can lead to serious damage to structures secondary to the obstructive lesion in the prostate (bladder hypertrophy, hydronephrosis, dilation of the kidney pelves, chronic infection, dilation of ureters, etc.), which is not without significant consequences. Also, a significant number of patients with symptoms sufficiently severe to warrant surgical intervention are therefore poor operative risks and are poor candidates for prostatectomy. In addition, younger men suffering from BPH who do not desire to risk complications such as infertility are often forced to avoid surgical intervention. Thus the need, importance, and value of improved surgical and non-surgical methods for treating BPH are unquestionable.

High-frequency currents are used in electrocautery procedures for cutting human tissue, especially when a bloodless incision is desired or when the operating site is not accessible with a normal scalpel but presents an access for a thin instrument through natural body openings such as the esophagus, intestines or urethra. Examples include the removal of prostatic adenomas, bladder tumors or intestinal polyps. In such cases, the high-frequency current is fed by a surgical probe into the tissue to be cut. The resulting dissipated heat causes boiling and vaporization of the cell fluid at this point, whereupon the cell walls rupture, and the tissue is separated.

Ablation of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using an electromagnetic energy which is rapidly dissipated and reduced to a non-destructive level by conduction and convection forces of circulating fluids and other natural body processes.

Microwave, radio frequency (RF), acoustical (ultrasound) and light energy (laser) devices, and tissue destructive substances have been used to destroy malignant, benign, and other types of cells and tissues from a wide variety of anatomic sites and organs. Tissues treated include isolated carcinoma masses in organs such as the prostate, and glandular and stromal nodules characteristic of benign prostate hyperplasia. These devices typically include a catheter or cannula which is used to carry a radio frequency electrode or microwave antenna through a duct to the zone of treatment and apply energy diffusely through the duct wall into the surrounding tissue in all directions. Severe trauma is often sustained by the duct wall during this cellular ablation process, and some devices combine cooling systems with microwave antennas to reduce trauma to the ductal wall. For treating the prostate with these devices, for example, heat energy is delivered through the walls of the urethra into the surrounding prostate cells in an effort to ablate the tissue causing the constriction of the urethra. Light energy, typically from a laser, is delivered to prostate tissue target sites by "burning through" the wall of the urethra. Healthy cells of the duct wall and healthy tissue between the nodules and duct wall are also indiscriminately destroyed in the process and can cause unnecessary loss of some prostate function. Furthermore, the added cooling function of some microwave devices complicates the apparatus and requires that the device be sufficiently large to accommodate this cooling system.

Catheters with axial to angular lumen orientation were shown in Fogarty, U.S. Pat. No. 4,774,949, issued Oct. 4, 1988. Johnston et al, U.S. Pat. No. 4,709,698, issued Dec. 1, 1987, discloses a heatable dilation catheter where the position of the catheter is monitored externally from the patient's body.

OBJECTS AND SUMMARY OF THE INVENTION

It is one object of this invention to provide a device for penetrating tissue, through intervening tissues to the precise target tissue selected for a medical action such as tissue ablation and optional substance delivery, limiting this activity to the precise preselected site, thereby minimizing the trauma and achieving a greater medical benefit.

It is another object of the present invention to provide a medical probe device including additional stylet probes for extension from additional stylet ports into the target tissue to measure the temperature of the target tissue to monitor the progress and effectiveness of the ablation process under way.

In summary, this invention relates to a method and system for applying ablation power to a body organ comprising a catheter having a stylet guide housing at the distal end thereof, said guide housing having one or more stylet ports for directing flexible stylets outward through intervening tissue to target tissue; said flexible stylets comprising a first group of stylets and a second group of stylets. The first group of stylets comprise active stylets for emitting electromagnetic energy, said electromagnetic energy being delivered as ablation power to said target tissue;and said second group of stylets comprising passive stylets for measuring the temperature of the target tissue. The system further includes a handle coupled to said catheter for gripping by an operator, a first set of deployment members on said handle for selectively deploying said first set of stylets into said target tissue; and a second set of deployment members on said handle for selectively deploying said second set of stylets into said target tissue.

Further, the system further includes an electromagnetic energy generator for generating said electromagnetic energy, said generator being coupled to said first group of stylets on said catheter; and temperature display apparatus coupled to said second group of stylets to monitor and display the temperature sensed by said second group of stylets. The system also includes an ultrasound probe for providing information relating to the position of the first and second groups of stylets when situated adjacent to the desired body organ, and a set of temperature sensors mounted in operational relationship with said ultrasound probe to monitor the temperature of body tissue immediately adjacent to the operating end of said ultrasound probe with a manual switch for selectively enabling said electromagnetic energy generator to deliver said electromagnetic energy to said first group of stylets; and a grounding plate coupled to said RF generator for providing a return path to said RF generator for said electromagnetic energy.

This embodiment also sets forth that flexible stylets comprise electrical conductors; and wherein said first set of deployment members are individually activated to position one or more of said first set of stylets in said target tissue; and said second set of deployment members are individually activated to position one or more of said second set of stylets in said target tissue, wherein said first set of deployment members comprise a plurality of sliders mounted on said handle and coupled to said first set of stylets for longitudinal movement in the handle and catheter to deploy a selected portion of the electrical conductor surface of each stylet in the target tissue; and wherein said second set of deployment members comprise a plurality of push-pull handles on respective sliders in operating relationship with said handle and coupled to said second set of stylets for longitudinal movement in the handle and catheter to deploy a selected portion of each stylet in the target tissue. The second set of stylets each comprise a temperature sensor mounted on said stylet immediately rearward of the distal end of said stylet and insulated therefrom by a separating insulating layer on the electrical conductor of said stylet wherein said temperature sensors are mounted on a condom placed over the operating end of said ultrasound probe such that as said ultrasound probe is positioned adjacent the area of target tissue, the temperature sensors are in a position to monitor the temperature in the immediate region encompassing said ultrasound probe. This system further includes a second condom which is placed over said first-mentioned condom to protect the temperature sensors from accidental displacement during the positioning of the ultrasound probe. Here the sensors are positioned on a tape or other adhesive backed flexible surface to be affixed to said first-mentioned condom.

Also described herein is a method of heat treatment of a target tissue without exposing tissue surrounding said target tissue to destructive temperatures, comprising the following steps. Introducing a catheter to a position adjacent to said target tissue and deploying a first flexible stylet out from said catheter into said target tissue. Delivering through said first flexible stylet electromagnetic energy to said target tissue. Maintaining said electromagnetic energy at an energy level and for a time sufficient to ablate said target tissue. Deploying a second flexible stylet out from said catheter into said target tissue to monitor the temperature of said target tissue proximate to said second flexible stylet. And utilizing the measured temperature to control the application of said electromagnetic energy to said first stylet. The disclosed method further includes monitoring the location of said catheter ultrasonically, wherein the step of ultrasonic monitoring further includes manipulating the ultrasonic probe to a position adjacent the target tissue, wherein the step of deploying the second flexible stylet includes providing a temperature sensor on said stylet immediately rearward of the distal end of said stylet. The method further includes providing temperature sensors in operating relationship with said ultrasound probe to provide temperature information in the area immediately proximate to the operating end of said ultrasound probe, and measuring the temperature in the area immediately adjacent to the distal end of said catheter.

Included in the invention is a stylet comprising an extended, wirelike member having at least one sharpened end; with a temperature sensor mounted immediately rearward of the sharpened end of said member, said temperature sensor being surrounded by a first heat shield, and a second heat shield surrounding said temperature sensor and said first heat shield and said member except at the sharpened end thereof.

An embodiment of the present invention also includes a temperature sensor apparatus for use in the measurement of temperature about the distal end of said apparatus which comprises an extended hollow tube having a proximal end and a distal end, an electrical connector mounted on the proximal end of said apparatus, and a heat shrink apparatus surrounding the proximal end of said apparatus to provide strength and strain protection to the hollow tube immediately adjacent the electrical connector. Further included in this embodiment are temperature sensors mounted on the hollow tube at and rearward of the distal end thereof, and a flexible tape member mounted at the distal end of said hollow tube, said tape member having at least one surface with a sticky or adhesive substance thereon. Additionally disclosed are electrical conductors in the hollow tube for connecting the electrical connector to the temperature sensors.

A temperature sensor apparatus is also disclosed for use in the measurement of temperature about the distal end of said apparatus comprising a condom, and an extended electrical cable, having a proximal end and a distal end, affixed to said condom in the longitudinal direction of said condom, said distal end of said electrical cable comprising a plurality of temperature sensors. Further included in this embodiment are an electrical connector mounted on the proximal end of said electrical cable, and a heat shrink apparatus surrounding the proximal end of said apparatus to provide strength and strain relief protection to the electrical cable immediately adjacent the electrical connector. The temperature sensors could be mounted on the closed end of said condom, while the electrical cable is mounted in a longitudinal groove in said condom, and the host device upon which the condom is mounted is an ultrasound probe.

BRIEF DESCRIPTION OF THE DRAWINGS

FIG. 2 is an isometric view of an RF ablation catheter embodiment with deployment apparatus for three additional temperature measurement stylets;

FIG. 3 is an isometric view of the distal end of the ablation catheter of FIG. 1 showing the additional temperature measurement stylets in detail;

FIG. 4 is a side view of the ablation catheter embodiment of FIG. 2;

FIG. 5 is a side view of the ablation catheter of FIG. 2 with a cross-sectional view of the three temperature measurement stylet deployment handle apparatus;

FIG. 10 is a top view of the temperature measurement assembly which would be attached to a condom surrounding an ultrasound probe;

FIG. 11 is a top expanded view of the distal end of the thermocouple assembly of FIG. 10.

DETAILED DESCRIPTION OF THE INVENTION

Figure 1:
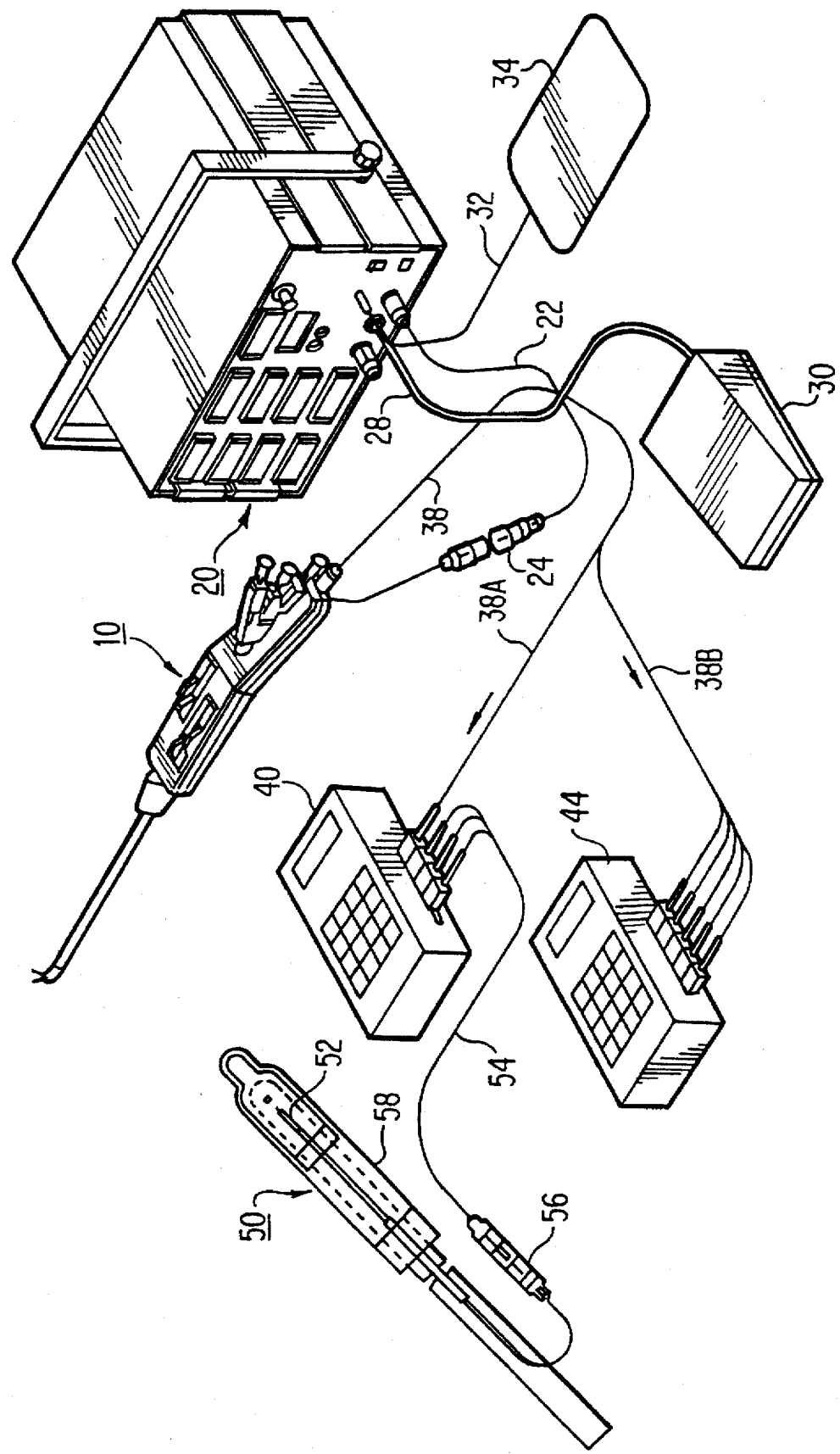
FIG. 1 is an isometric view of the entire system in which the RF ablation catheter is the operating device.

The device of this invention provides a precise controlled positioning of a treatment stylet in a tissue targeted for treatment, ablation, or sampling from a catheter positioned in the vicinity of targeted tissues.

The term "stylet" as used hereinafter is defined to include both solid and hollow probes which are adapted to be passed from a catheter port through normal tissue to targeted tissues. The stylet is shaped to facilitate easy passage through tissue. It can be a solid wire, thin rod, or other solid shape or it can be a thin hollow tube or other shape having a longitudinal lumen or lumens for introducing fluids to or removing materials from a site. The stylet can also be a thin hollow tube or other hollow shape, the hollow lumen thereof containing a reinforcing or functional rod or tube such as a laser fiber optic. The stylet preferably has a sharpened end to reduce resistance and trauma when it is pushed through tissue to a target site.

The stylet can be designed to provide a variety of medically desired treatments of a selected tissue. As a resistance heater, radio frequency electrode, laser light emitter, or microwave antenna, it can be used to ablate or destroy targeted tissues. As a hollow tube, it can be used to deliver a treatment fluid such as a liquid to targeted tissues. The liquid can be a simple solution or a suspension of solids, for example, colloidal particles, in a liquid. Since the stylet is very thin, it can be directed from the catheter through intervening normal tissue with a minimum of trauma to the normal tissue.

The device and method of this invention provide a more precise, controlled medical treatment which is suitable for destroying cells of medically targeted tissues throughout the body, both within and external to body organs. The device and method are particularly useful for treating benign prostate hyperplasia (BPH), and the device and its use are hereinafter described with respect to BPH, for purposes of simplifying the description thereof. It will be readily apparent to a person skilled in the art that the apparatus and method herein can be used to destroy body tissues in any body cavities or tissue locations that are accessible by percutaneous or endoscopic catheters, and is not limited to the prostate. Application of the device and method in all of these organs and tissues are intended to be included within the scope of this invention.

BPH is a condition which arises from the benign replication and growth of cells in the prostate, forming glandular and stromal nodules which expand the prostate and constrict the opening of the prostatic urethra. Glandular nodules are primarily concentrated within the transition zone, and stromal nodules within the periurethral region. Traditional treatments of this condition have included surgical removal of the entire prostate gland, digital removal of the adenoma, as well as transurethral resection of the urethral canal and prostate to remove tissue and widen the passageway. One significant and serious complication associated with these procedures is iatrogenic sterility. More recently, laser treatment has been employed to remove tissue, limiting bleeding and loss of body fluids. Balloons have also been expanded within the urethra to enlarge its diameter, with and without heat, but have been found to have significant limitations.

One embodiment of the device of this invention previously disclosed in a parent application uses the urethra to access the prostate and positions RF electrode stylets directly into the tissues or nodules to be destroyed. The portion of the stylet conductor extending from the urethra to targeted tissues is enclosed within a longitudinally adjustable sleeve shield which prevents exposure of the tissue adjacent to the sleeve to the RF current. The sleeve movement is also used to control the amount of energy per unit surface area which is delivered by controlling the amount of electrode exposed. Thus the ablation is confined to the tissues targeted for ablation, namely those causing the mechanical constriction. Other aspects of the invention will become apparent from the drawings and accompanying descriptions of the device and method of this invention. It will be readily apparent to a person skilled in the art that this procedure can be used in many areas of the body for percutaneous approaches and approaches through body orifices.

FIG. 1 is an isometric view of the entire system utilizing the RF ablation catheter herein. In the center of FIG. 1 is the ablation catheter 10 of the present invention. The RF supply source 20 is the RF power generator as fully set forth in copending application Ser. No. 08/061,072, filed May 14, 1993 and, as set forth above, the entire contents of which are herein incorporated by reference. The RF power line 22 plugs into the RF generator 20 and to the input terminal on the handle of the ablation catheter. A quick connect device 24 may be supplied to allow for easier connection to the RF power source 20 as may be provided for the convenience of the operating surgeon. Another input into the RF power generator 20 is the connection 28 from the foot operating switch 30. The surgeon would depress this switch with his or her foot after the ablation catheter 10 is in operating position. The last input to the RF generator is the connection 32 from the external grounding plate 34 which is used as a return path for the RF current passed into the body tissue upon activation by the surgeon operator. As set forth above, the grounding plate, well known in the prior art, should be big enough to dissipate the RF current flowing in the body so as to prevent burning by the localization of the return RF current.

There are six thermocouple signals that are to be detected after stylet deployment, as will be shown below in conjunction with FIG. 3. The two active RF stylets each have thermocouples mounted adjacent the sharp stylet tip. Each of the three temperature sensing stylets have a thermocouple (or other temperature measuring device), plus there is one in the body of the distal end of the catheter adjacent the ports from which the stylets, both active and RF, are deployed. All stylets, except for the thermocouple mounted in the catheter body and not on a stylet, are selectively deployable at the option of the operator. The six thermocouple signal leads from the ablation catheter are shown schematically for ease of understanding to be a single lead 38 until near the destination of the leads. In this embodiment, the lead 38A from the thermocouple in the body of the catheter near the distal end thereof, is attached to one input T1 of the Data Logger B monitoring apparatus 40. The other five thermocouple leads from the ablation catheter 10 are connected to the input terminals T1, T2, T3, T4, and T5, respectively of Data Logger A 44. In this embodiment, the forward most temperature monitoring stylet is connected to terminal T4 of Data Logger A. The middle stylet is connected to terminal T3 of Data Logger A; while the innermost stylet is connected to terminal T5 of the Data Logger A. One of the active RF stylets is connected to terminal T1 of Data Logger A, while the other active RF stylet is connected to terminal T2 of the Data Logger A.

The Data Loggers A, designation 44, and B, designation 40, are commercial temperature recording devices marketed under the Trade name Data Logger. The other inputs to the Data Logger B are from a separate ultrasound probe 50 upon which is mounted additional temperature detectors such as thermocouples. The ultrasound probe 50 is utilized by the operating surgeon to monitor the placement of the active stylets and the temperature measurement stylets into the desired tissue. In this embodiment, the target tissue is the human prostate gland, but as set forth previously, other body glands and/or tissue could be targeted as well.

FIG. 2 is an isometric view of an ablation catheter 10 of this invention with provisions for three extra temperature measurement stylets 204, 206, and 208, in addition to the active stylets 210 and 212, as seen more clearly in FIG. 3. The flexible catheter 202, attached to handle 214, has a terminal stylet guide 216 with two active RF stylets 210 and 212. The handle 214 has stylet sleeve tabs 216 and 218, and stylet electrode tabs 220 and 222, as will be described in greater detail hereinafter. The handle 214 is also connected to an RF power connector, and thermocouple connectors 20 (seen below in FIG. 6). The portions of the catheter 202 leading from the handle 214 to the stylet guide tip 21 6 can optionally have a graduated stiffness. For example, the catheter can be designed to be more stiff near the handle (proximal end) and more flexible near the tip (distal end), or any other stiffness profiles. The catheter 202 can be constructed of an inner slotted stainless steel tube with outer flexible sleeve such as is described in copending application Ser. No. 790,648 filed Aug. 11, 1991 (corresponding to published Australian patent application Ser. No. 9210858), the entire contents of which are incorporated herein by reference. It can also be made of coiled or braided wire to which an outer sleeve is bonded.

FIG. 3 is an isometric view of a preferred catheter tip and stylet guide housing of this invention. With like items having the same numerical designations, the solid catheter tip 216 or 'bullet' end of the catheter has, in this embodiment, five stylet ports, from which stylet assemblies can be deployed. Only two stylet ports 208a for stylet 208 and 212a for stylet 212 are seen clearly in this figure. However, all five stylets have accompanying stylet ports from which the stylets are deployed. The two stylets 210 and 212 protruding from the catheter end 215 at predetermined angles are the active stylets from which radio frequency RF energy is emitted upon activation. The other three stylets 204, 206, 208 along the longitudinal axis of the catheter 202 and between stylets 210 and 212 are the temperature measurement stylet assemblies. These temperature measurement stylets have thermocouples mounted on them (See FIG. 7 below) in order to measure the temperature of the tissue into which these stylets are deployed. Stylers 210 and 212 are the active RF stylets. That is, upon activation by the operating surgeon, RF energy is applied to the stylets 210, 212 after they are deployed into the target tissue. The RF stylets operate in a unipolar mode. That is, the RF energy is applied to one or both of the stylets with the RF current flowing into the living body in which the apparatus is applied. An external grounding plate 34 (See FIG. 1) is used as the return electrode. This grounding plate is large enough to absorb all of the RF current flowing from the RF stylets so as not to burn the patient upon whom the device is operating. The RF stylets 210, 212 could, if desired, operate in a bipolar mode where RF energy is emitted from one stylet with the current return being provided by the other stylet. No external grounding plate would be necessary in this instance.

Also in FIG. 3 are the three temperature measurement stylets 204, 206, 208. These stylets would be deployed by the operating surgeon when he or she desires to monitor the temperature of the target tissue being ablated. The stylets have mounted on them tiny thermocouple devices which will measure the temperature of the tissue immediately surrounding the stylets. The active stylets 210, 212 as well as the temperature monitoring stylets 204, 206, 208 are selectively deployable by the operating surgeon. That is, all or individual ones can be selectively deployed at the option of the operator. A temperature measuring device, also a thermocouple, is mounted in the catheter tip 216, to measure the temperature of the environment surrounding the catheter tip while the ablation procedure is proceeding at the tips of the RF stylet electrodes. The three temperature monitoring stylets 204, 206, 208 could also be active stylets and be connected to an RF source as are stylets 208 and 210, but in this embodiment they will continue to be described as if they are only temperature monitoring stylets, as shown in FIG. 3.

FIG. 3 illustrates two active RF stylets and three temperature measurement stylets. But it would be apparent to one skilled in this art, that the number of active stylets and RF stylets is a matter of choice, as more or less stylets may be used within the teachings of the present invention.

In operation, the surgeon would insert the ablation catheter 10 into the patient's urethra. The catheter would be inserted as far up the urethra as necessary to place the operating end 216 of the ablation catheter in the urethra adjacent the prostate gland tissue to be ablated. The slide handles 220, 222 on the ablation catheter's handle would be moved forward which would move the active RF stylets out of their respective ports on the distal end of the catheter. The stylets would move out of the catheter, through the wall of the urethra into the target tissue, here the prostate. Slide handles 216 and 218 would be withdrawn at this time to uncover the active ends of the stylets to control the amount of RF current to be employed to begin the ablation process. If the operator at this-time desires to monitor the temperature of the target tissue while the ablation is taking place, the three temperature monitoring stylets 204, 206, 208 (all or any combination of the three stylets) would also be deployed at this time via the movement of handles 224, 226, 228 on slider assembly 229. The temperature monitoring stylets 204, 206, 208 would be deployed by respective movement of the sliders 230, 232, 234 on the extension mounted on the handle. The slider assembly 229 has a vernier gradient 236, 238, 240 etched in the side for each slider 230, 232, 234 so that the operator may accurately deploy the temperature measurement stylets into the target tissue as desired. After the stylets (or some of them) are deployed, the operator depresses the foot operating pedal switch 34, in FIG. 1, to apply the RF current signal to the RF stylets 210, 212. How long the RF current is applied and how deep the stylets are deployed into the target tissue depend on the size and depth of the area to be ablated.

Information that the operator uses to decide how long to apply the current and the amount of current to be applied is determined by monitoring the temperature of the tissue as it is being ablated. Thus, the Data Loggers 40 and 44 monitor and display the temperatures being detected by the thermocouple detectors. There are six sensors on the distal end of the catheter, two in the active RF stylets 210, 21 2, three in the temperature measurement stylets 204, 206, 208, and one 211 in the distal end of the catheter body 216. If the surgeon desires additional readings, the ultrasound probe 50 in FIG. 1 could be outfitted with three or any other number of thermocouples as well. That is, the ultrasound device 50 is used by the surgeon to accurately place the stylet end of the catheter in the desired position adjacent the tissue to be ablated in the prostate. The ultrasound probe would be inserted in the rectum of the patient and operated, as known in the prior art, to detect the movement and placement of the operating end of that ablation catheter. When the ultrasound operator decides that the catheter probe is in the right position for the ablating operation to commence, this information is conveyed to the operating surgeon who then decides how long and how much current to apply.

Mounted on the ultrasound probe 50 are the additional temperature monitoring sensors 52 for additional input to the Data Loggers. The temperature information is transferred to input terminals P1, P2, P3 of the Data Logger 40 via leads 54 in FIG. 1. Quick disconnector 56 allows the surgeon to connect the ultrasound unit at the patient rather than at the electronic units. With the input information regarding temperature of the tissue being ablated, plus the temperature of the urethra at the distal end of the ablation catheter, together with the temperature of the rectum tissue detected by the sensors on the ultrasound probe, the operating surgeon now has enough information to decide how much RF current to apply, as well as how long to apply it.

FIG. 4 is a side view of the ablation catheter 10 showing the temperature measurement stylets 204, 206, 208 being deployed, as well as the deployment handles 224, 226, 228 for deploying the temperature sensor stylets and measuring the site temperature. FIG. 4 illustrates the catheter including the slider assembly 229 for deploying the temperature monitoring stylets. Handle 214 is connected to the flexible catheter 202. At the distal end of the catheter 202 is the catheter end unit 215 and the deployed temperature sensor stylets 204, 206, and 208. From this side view, the stylet ports for the three temperature sensor stylets cannot be seen. However, stylet port 212a for the RF stylet electrode 212 is visible and, for ease of viewing, stylet 21 2 has been omitted from this figure. At the proximal end of the unit 10, is the support connector 242. In previous embodiments disclosed in the parent applications cited above and herein incorporated by reference, this support connector included the optical viewing apparatus which a surgeon or other operator would utilize to view the operating end of the catheter via fiber optics when deployed within a patient. The optical fibers would extend from the handle assembly at the proximal end to the catheter end unit at the distal end in lumens within the handle and flexible catheter. In this embodiment, however, to provide for extra temperature sensing, the control apparatus and stylet lengths themselves utilize the support connector and the catheter lumens in which the optics formerly occupied, but now are occupied by the stylet electrodes and cables.

Slider assembly 229 is attached to the support connector where the optical viewing apparatus used to be. With three temperature monitoring and measuring stylets 204, 206, 208 being utilized in this embodiment, there are three temperature stylet deployment handles 224, 226, 228, one for each stylet tip. Each handle is attached to a stylet assembly slider 230, 232, 234, respectively, which are frictionally attached to the slider assembly 229. The stylet lengths are attached internally to the sliders by extensions visible in FIG. 5. When the surgeon desires to deploy the temperature measurement stylets 204, 206, or 208, the handles 224, 226, or 228 are selectively pushed toward the distal end of the ablation catheter assembly 10. This pushes each individual stylet through its respective lumen within the catheter 202 and forces it out the respective stylet port. The length of deployment is measured by the surgeon by the vernier gradients 236, 238, or 240, as seen in FIG. 2.

FIG. 5 is a side view of the ablation catheter handle 10 with the support connector 242 shown in cross-section. The innermost temperature sensor stylet 208 is shown attached to handle 224; while, not shown, are stylet 206 connected to handle 226, and stylet 204 is connected to handle 228. Stylet 208 is in its particular lumen in flexible catheter 202 and passes through handle 214 to the support connector 242. The stylet 202 passes through the slider assembly 229 and is attached to collet screw 250 via collet nut 252. Styler handle 224 is attached to the collet nut to provide a grasping handle for the surgeon. The handle would also be made of an insulating plastic or other material to prevent any spurious RF current from being transferred to the operating surgeon.

Figure 6:
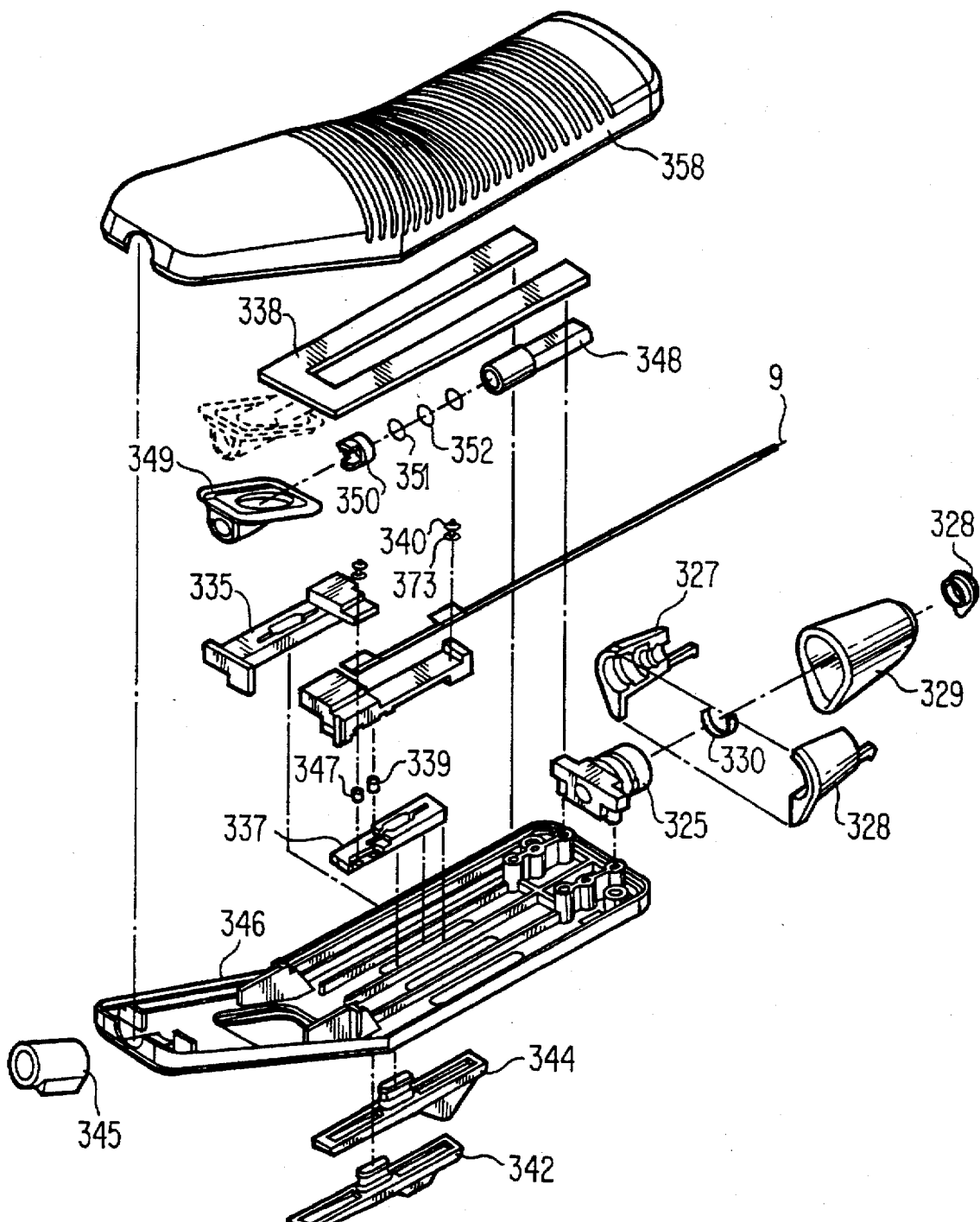
FIG. 6 is an exploded view of the temperature measurement handle apparatus of FIG. 5.

FIG. 6 is a breakaway drawing of the assembly shown and described in conjunction with FIGS. 4 and 5. The embodiment in this figure is shown upside down because of the unique aspects of the assembly and is more revealing in this configuration. Bottom handle 358 and upper handle 346 are shown separated with the internal components in between. The electrical connector housing 345 is connected at the rear of the handle assembly 10 and is the connection to the rest of the system as shown and described in FIG. 1 for the RF energy to the stylets and the return path for the electrical leads from the temperature sensors in the active stylets as well as those in the additional temperature sensor stylets and the temperature sensor in the body of the catheter at the distal end thereof. The front of the handle comprises the twist control knob 329 and twist knob cap 328 connected to the handle 10 by use of the right split sleeve 327 and the left split sleeve 326; utilizing a twist knob spring 330 and twist tube block 325. The twist control knob is used by the surgeon to twist the catheter 90 degrees in either the right direction or 90 degrees in the left direction so that the handle can be held in a comfortable position by the surgeon, and allow him or her to rotate the operating distal end of the catheter within the patient prior to deploying the stylets accurately into the target tissue.

To simplify FIG. 6, only two of the four deployment sliders for the active RF stylets are shown. Control slide 344 controls the movement and deployment of the RF stylet electrode; while the control slide 342 controls the movement of the insulating sleeve on the stylet electrode. That is, after the RF stylet is deployed by the surgeon, the insulator slide 342 is retracted, thereby withdrawing the insulating sleeve away from the sharp tip of the RF stylet. The more the sleeve is withdrawn, the more stylet electrode is exposed to the surrounding tissue, thereby allowing more RF current to flow in the ablation action. The top of the catheter handle 10 would also have a vernier scale to assist the surgeon in accurate measurement of both the stylet depth into target tissue, as well as the length of stylet exposed to the tissue for RF current transfer and flow. The slide handles are assembled in the handle by means of locking slide member 337, compression spring 347, friction pad 339, and insulating slide 335. The RF stylet electrode needle 399 is attached to this assembly via needle slide 333.

The support connector 242 in FIG. 5 is labelled as connector 349 in FIG. 6. This unit is attached to the handle assembly 10 by the use of O-ring retainer 350, O-ring 351, handle washers 352, friction block 338, and shaft receiver 348.

Figure 7A:
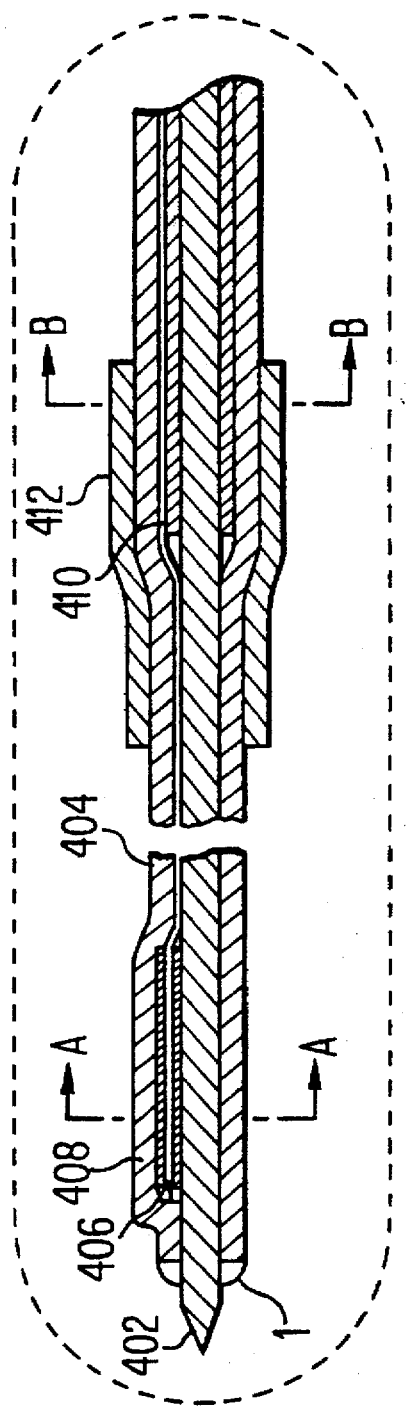
FIG. 7A is a cross-sectional view of a temperature measurement stylet.

FIG. 7A is a side cross-sectional view of one of the temperature measurement stylets of the present invention. Styler sensor 204 of FIG. 3 will be described here, but the description is valid for stylet sensors 206 and 208, as well. Stylet 402, of flexible nickel titanium wire, would extend the length of the ablation catheter from the proximal end at the stylet handles to the operating tip of the catheter at its distal end. Surrounding the entire length of the stylet 402 is a heat shrink sleeve 404, made of Kynar, for example. Immediately adjacent the distal end of the stylet, just rearward of the sharpened tip of the stylet, is the temperature sensor or thermocouple. The 34 AWG gauge thermocouple detects the temperature of its surroundings and due to the change in current flow, the Data Loggers can detect and convert the current flow into a temperature reading. The thermocouple is wrapped in a polyester heat shrink cover 408 to protect and shield it during manufacture. At a predetermined distance back from the distal end of the stylet sensor, the thermocouple wires are positioned away from the stylet. Also at this juncture, additional Kynar heat shielding is provided, also for longitudinal rigidity. At the very front of the stylet at its distal end right at the stylet-Kynar heat shield junction is an adhesive, which both prevents the stylet from moving within the Kynar heat shield, but also to prevent internal stylet contamination by body fluids.

Figure 7C:
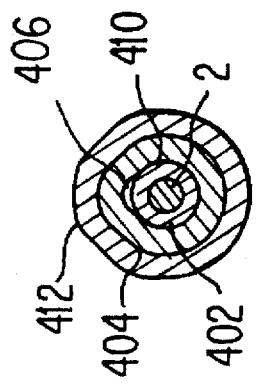
FIG. 7C is a cross-sectional view of the stylet through lines B—B.
Figure 7B:
FIG. 7B is cross-sectional view of the temperature measurement stylet along the lines A—A.

FIG. 7B is a cross-sectional proximal view of the stylet sensor 204 through lines A—A in FIG. 7A. In the center of FIG. 7A is the stylet sensor wire 402. Right above it is the thermocouple 406 surrounded by polyester heat shrink shield 408. Surrounding both the stylet 402 and polyester shield 408 is the Kynar heat shield 404. Also depicted in the background in FIG. 7A, but not part of the cross-section at lines A—A, is the Kynar heat shrink shield 412.

FIG. 7C is a cross-sectional view of the stylet sensor 204 through lines B—B in FIG. 7A. In the center of FIG. 7C is the stylet wire 402. Moving outwardly from the center, next surrounding the stylet wire 402 is the SST tube 410. On top of the SST tube are the thermocouple wires 406. Surrounding both the SST tube and the thermocouple sensor wires is the Kynar heat shrink 404. Lastly, surrounding everything at the cross-section is the additional Kynar heat shrink shield 412.

Figure 8B:
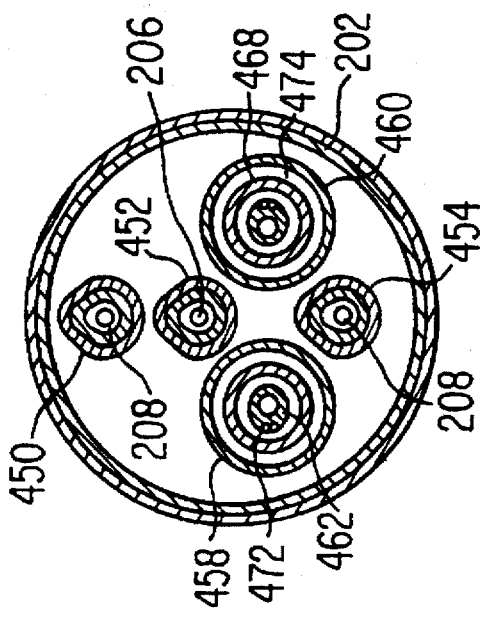
FIG. 8B is a cross-sectional proximal view of the mid-section region of the catheter of FIG. 4 taken along the lines D—D in FIG. 4.
Figure 8A:
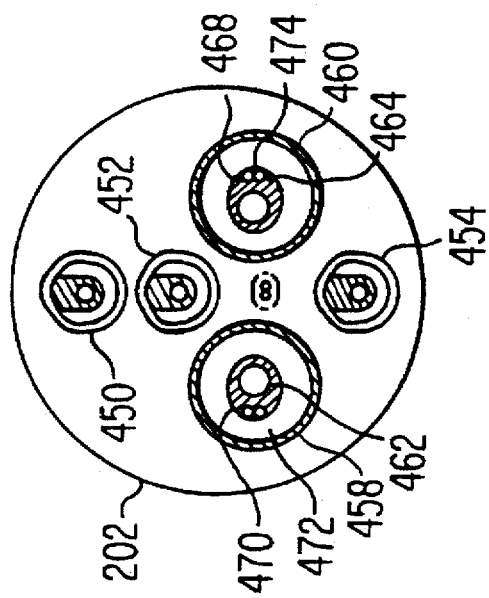
FIG. 8A is a cross-sectional proximal view of the distal region of the catheter of FIG. 4 taken along the lines C—C in FIG. 4.

FIG. 8A is a cross-sectional view of the distal end of catheter 202 immediately adjacent the ports from which the stylets are deployed taken along lines C—C in FIG. 4. Temperature sensor stylet lumens 450, 452, and 454 are shown in FIG. 8A as vertically oriented along the length of the catheter 202. In stylet lumen 450 is placed stylet 208, as seen in FIG. 3; while in stylet lumen 452 is placed stylet 208, and in stylet lumen 454 is placed stylet 208. Each of the stylet lumens is similar to the assembly shown and described in conjunction with FIG. 7B.

Also seen in FIG. 8A are the active stylet lumens 458 and 460. Surrounding each stylet electrode 462 and 464 are the insulating stylet sleeves 468 and 470. Adjacent each stylet electrode 462 and 464 and within the stylet sleeves 468 and 470 are thermocouples 472 and 474.

FIG. 8B is a cross-sectional view of the catheter 202 taken approximately half way between the handle of the catheter assembly and the distal end where the stylets are deployed taken along lines D—D in FIG. 4. Temperature sensor stylet lumens 450, 452, and 454 are similarly shown in FIG. 8B as vertically oriented along the length of the catheter 202. In stylet lumen 450 is placed stylet 208, as seen in FIG. 3; while in stylet lumen 452 is placed stylet 206, and in stylet lumen 454 is placed stylet 208. Each of the stylet lumens are similar to the assembly shown and described in conjunction with FIG. 7C.

Also seen in FIG. 8B are the active stylet lumens 458 and 460. Surrounding each stylet electrode 462 and 464 are the insulating stylet sleeves 468 and 470. Adjacent each stylet electrode 462 and 464 and within the stylet sleeves 468 and 470 are thermocouples 472 and 474.

Figure 9B:
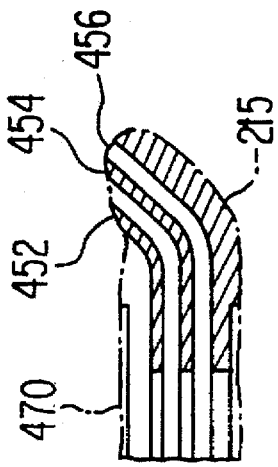
FIG. 9B is a cross-sectional view of the distal end of the side view of the catheter of FIG. 3 through the lines F—F in FIG. 9C.
Figure 9C:
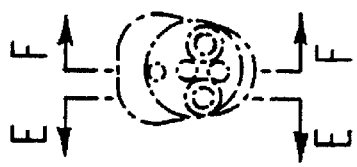
FIG. 9C is a schematic representation of FIG. 8A to show the view lines for FIGS. 9A and 9B.
Figure 9A:
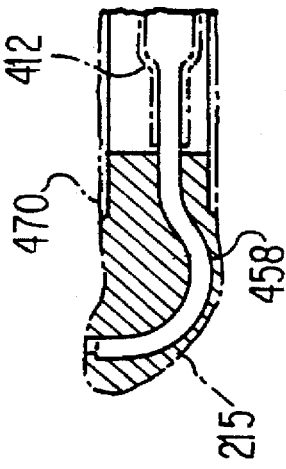
FIG. 9A is a cross-sectional view of the distal end of the side view of the catheter of FIG. 3 through the lines E—E in FIG. 9C.

FIG. 9A is a cross-sectional view of the distal end of the catheter so that the internal lumens for the various stylets are shown, along lines E—E in FIG. 9C. This view is along the line through the lumen for one of the active stylet electrodes. Active stylet 210 (see FIG. 2) would be in position in lumen 458, but is not shown in this figure to allow for a better depiction of the associated lumens. The insulating sleeve 470 is shown, as is the stylet insulating sleeve 412. The stylet electrode 210 (not shown) is snugly, but not tightly, axially movable in lumen 458. Thus, when the operating surgeon moves a stylet handle in the distal direction, the stylet and associated insulating sleeve are deployed out the front end of the distal end 215 of the catheter. This same description and apparatus also apply for the other active stylet electrode 212 seen in FIG. 3, but not in FIG. 9A.

FIG. 9C shows the distal end 215 through the lines F—F in FIG. 9C. This line is through the vertical line through the catheter end which depicts the three temperature sensor lumens. Lumen 452 would extend the length of the catheter until just before exiting the tip of the catheter. At the very tip, the lumen curves upwardly so that the stylet temperature sensor will be deployed at a predetermined angle. Lumen 454 is just below lumen 452 and exits the distal end of the stylet just in front of the lumen 452. Lumen 456 is just below lumen 454 and it exits the catheter end just in front of lumen 454. The lumens could all exit the catheter at the same angle or at slightly different angles, depending on the dispersion sought.

FIG. 10 is a top view of one embodiment of the temperature and thermocouple sensor arrangement 52 which is used in conjunction with an ultrasound probe. At the proximal end of the sensor arrangement is a standard electrical coupler 386 for use in attachment to Data Logger 40. A hollow tube 389 made of Pebax extends out from the connector 387 to the distal end thereof where the temperature sensors in the form of thermocouples are mounted. Surrounding the Pebax tubing 389 at the proximal end of the sensor arrangement 52 is a heat shrink tubing 387 for support and strength. Spiral wrap 357 acts as a tension relief at the connector 386. Slip sheath tubing 391 allows movement of the sensors on the tubing 389 of the ultrasound probe as will be hereinafter described.

FIG. 11 is an exploded view of the distal end of the sensor arrangement of FIG. 10. At the very distal end is a tape, such as bandage tape 390, for example, upon which is mounted the thermocouple wires 388 to direct the temperature readings to the Data Logger 40. One thermocouple sensor is placed at this point and two or more others 388A and 388B are positioned about one centimeter apart along the longitudinal axis of the sensor arrangement 52. Thus, whatever temperature is detected by these thermocouple sensors are transferred back to the Data Logger 40 via electrical leads in the hollow core of the Pebax tubing 389.

The sensor arrangement would be used, as set forth above in conjunction with an ultrasound probe 50, FIG. 1. A standard condom 58 would be placed on the end of the ultrasound probe 50 to allow for antiseptic application as well as for ease of entry. The sensor arrangement 52 would be positioned on the condom with the Pebax tubing running along the longitudinal axis of the ultrasound probe. When the sensor arrangement is positioned as desired along the ultrasound probe, with the thermocouple sensors adjacent the end of the ultrasound probe, the bandage tape end of the sensor arrangement is pressed onto the condom by the operating surgeon into position. Then another condom would be applied to the ultrasound probe over the first condom to protect the sensor arrangement and thermocouple from movement upon insertion of the ultrasound probe into the rectum of the patient. The probe can be positioned in the rectum by the ultrasound operator to give the best ultrasound picture of the ablation catheter's position in the patient's urethra.

Figure 12:
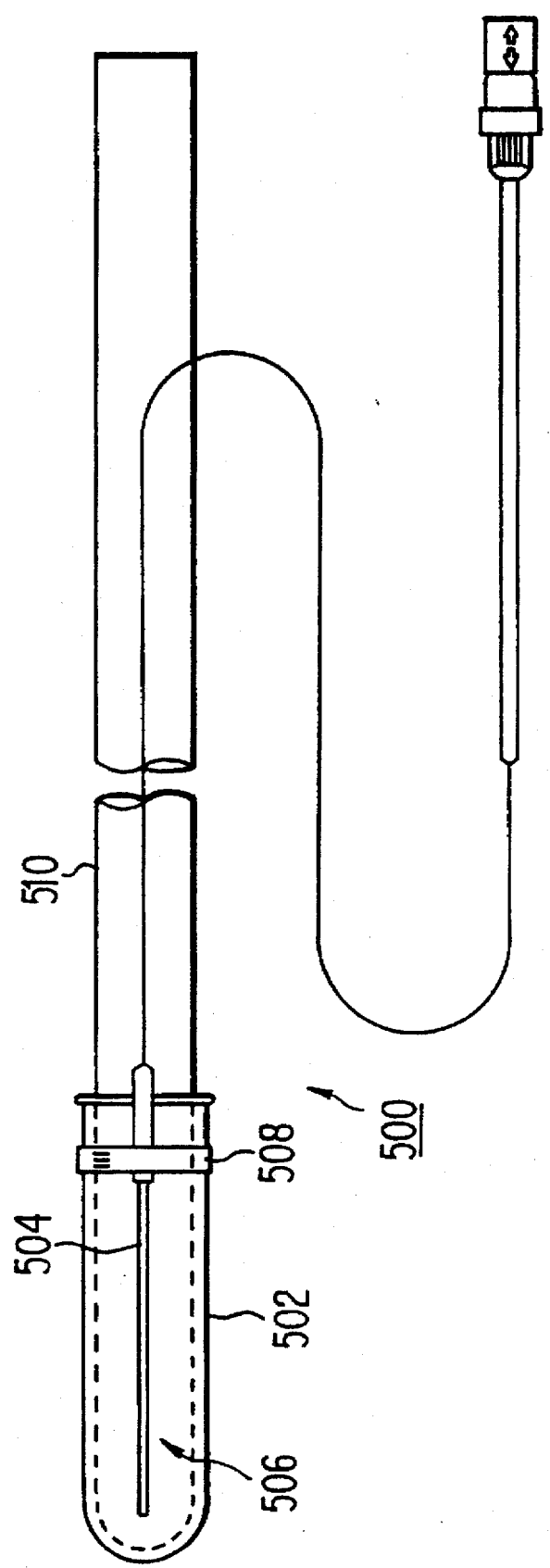
FIG. 12 is a cross-sectional view of an alternative embodiment of a thermocouple mounted condom and ultrasound probe.

An alternate and preferred arrangement for the sensor arrangement to be mounted on an ultrasound probe is shown and described in conjunction with FIG. 12. In this embodiment, the condom 500 is custom manufactured with a groove 504 in the condom. This groove is made in the condom along the longitudinal axis of the condom to receive the sensor arrangement 506. This arrangement has the top (away) side thereof with thermocouples already mounted on the bandage or similar strip. The sensor arrangement is placed in position and the adhesive on the reverse is pressed onto the special condom 502. The premanufactured groove 504 allows for the accurate placement of the sensor arrangement on the condom. The proximal end of the condom has a Velcro or similar type of attachment device 508 to hold the sensor arrangement 506 to the condom 502 during the insertion and removal of the ultrasound probe 510. If desired, and preferably, a second condom is placed over the first condom to allow easier insertion of the ultrasound probe.

In each of the embodiments utilizing the ultrasound probes and condoms, the commercial brand of KY Jelly could be used as lubrication for placing the first condom on the ultrasound probe, or the placement of the second condom over the first condom, as well as in use when insertion into the patient's body. Also, provisions can be made for insertion or inflation of saline or other solutions which may be necessary or desirable in the ultrasound process.

For purposes of illustration, but not by way of limitation, the prostate has been selected for this explanation, and application of this method and assembly to other areas of the body are intended to be included.

Although preferred embodiments of the subject invention have been described in some detail, it is understood by those skilled in the art, that obvious variations can be made herein without departing from the spirit and scope of the invention as defined by the appended claims.

We claim:

1. A medical device, comprising an ultrasound probe having a distal end portion for insertion into a body, a first condom mounted over the distal end portion of the ultrasound probe, a second condom mounted over the first condom, and a temperature sensor positioned between the two condoms for monitoring temperature within the body near the probe.

2. The medical device of claim 1 wherein the temperature sensor is adhesively affixed to the outer surface of the first condom.

3. The medical device of claim 1 wherein the temperature sensor is held in position between the two condoms by a Velcro-type fastener.

4. A medical device, comprising an ultrasound probe having an elongated distal end portion for insertion into a body, a first condom mounted over the distal end portion of the ultrasound probe and having a longitudinally extending groove opening through the outer surface thereof, a temperature sensor affixed to the outer surface near the groove, and an electrical cable connected to the temperature sensor and disposed in the groove.

5. The medical device of claim 4 including a second condom mounted over the first named condom and the temperature sensor.

6. The medical device of claim 4 wherein the temperature sensor is affixed to the outer surface of the condom by a Velcro-type fastener.

7. A medical device, comprising an ultrasound probe having an elongated distal end portion for insertion into a body, a condom mounted over the distal end portion of the ultrasound probe, a temperature sensor affixed to an outer surface of the condom, and an electrical cable extending proximally from the temperature sensor.

8. The medical device of claim 7 including a second condom mounted over the first named condom and the temperature sensor.

9. The medical device of claim 7 wherein the temperature sensor is adhesively affixed to the outer surface of the condom.

10. The medical device of claim 7 wherein the temperature sensor is affixed to the outer surface of the condom by adhesive tape.

11. The medical device of claim 7 wherein the temperature sensor is affixed to the outer surface of the condom by a Velcro-type fastener.

* * * * *